United States Patent [19]

Sato et al.

[11] 4,214,591
[45] Jul. 29, 1980

[54] BRAIN WAVE ANALYZING SYSTEM AND METHOD

[75] Inventors: Kensuke Sato, Nagayo; Kenji Ono, Isahaya, both of Japan

[73] Assignee: Foundation for the Medical Research on the Traffic Accident and Disaster, Tokyo, Japan

[21] Appl. No.: 897,411

[22] Filed: Apr. 18, 1978

[30] Foreign Application Priority Data

Oct. 8, 1977 [JP] Japan ................................. 52-121109

[51] Int. Cl.² .............................................. A61B 5/04
[52] U.S. Cl. .................................................. 128/731
[58] Field of Search ............................. 128/2.1 B, 731

[56] References Cited

U.S. PATENT DOCUMENTS 3,623,477  11/1971  Trent ................................. 128/2.1 B

OTHER PUBLICATIONS

Itil et al., "Electroencephalography and Clinical Neurophysiology", vol. 27, 1969, pp. 76-83.
Ueno et al., "Memoirs of the Faculty of Engineering Kyushu University", vol. 34, No. 3, Feb. 1975, pp. 195-209.
Gevins et al., "Proceedings of the Institute of Electrical and Electronic Engineers", vol. 63, No. 10, Oct. 1975, pp. 1382-1398.

Primary Examiner—William E. Kamm
Attorney, Agent, or Firm—Frishauf, Holtz, Goodman & Woodward

[57] ABSTRACT

A memory unit stores, as decision-criterion data for a brain wave to be examined, a mean vector A, a variance vector C and at least one critical value $F_\alpha$ at an appropriate significant level $\alpha$ obtained from F-distribution, the mean vector A being the mean value of autoregressive coefficient vectors calculated by a data operation and processor unit from respective brain waves of a standard brain wave group consisting of K number of standard brain waves, the variance vector being calculated from the mean vector and the autoregressive coefficients. An L-dimensional row vector X of the brain wave to be examined is calculated by the data operation and processor unit from the autoregressive coefficients of the brain wave to be examined. The distance $F_X$ between the row vector X and the mean vector A is also calculated. Further, the value of the distance $F_X$ is compared with the significant level $F_\alpha$ to determine whether or not the pattern of the brain wave to be examined has a significant level different from that of the standard brain wave group.

8 Claims, 15 Drawing Figures

FIG. 1A: EEG OF A NORMAL ADULT DERIVED BY Fz-Pz LEAD
FIG. 1B: AUTOREGRESSIVE POWER SPECTRUM CORRESPONDING TO FIG. 1A (REAL LINE) SPECTRUM COMPONENTS (DOTTED LINE)
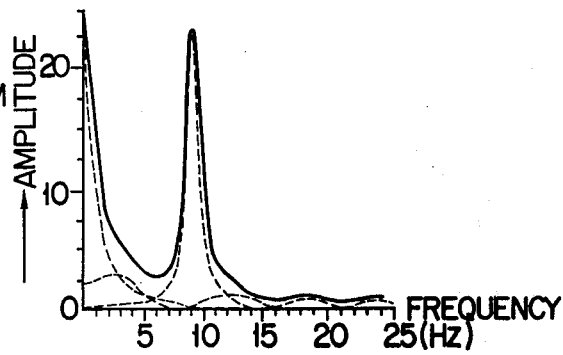
FIG. 2
ABSCISSA:
  STANDARDIZED AUTOREGRESSIVE COEFFICIENT
ORDINATE:
  CUMULATIVE FREQUENCY DISTRIBUTION (%) OF AUTOREGRESSIVE COEFFICIENT
$a_1$ TO $a_8$:
  FIRST TO EIGHTH ORDER AUTO-REGRESSIVE COEFFICIENT
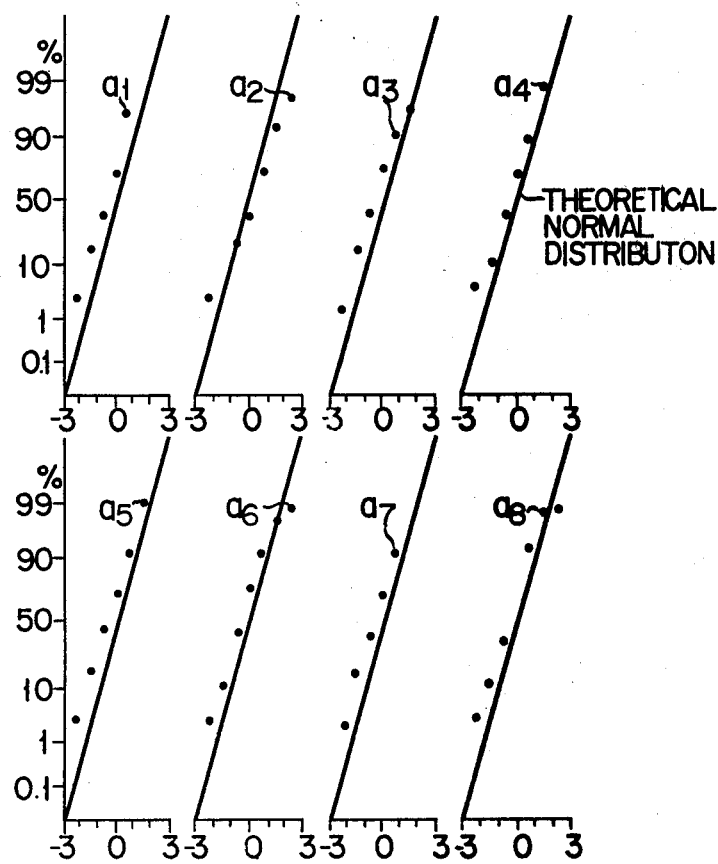

DISTRIBUTION(%)(ORDINATE) OF DISTANCE(Fx)(ABSCISSA)
FROM AVERAGE PATTERN(FIG.4A, FIG.4B, FIG.4C)
FIG. 4A
NORMAL EEG
GROUP(CONT) N=90
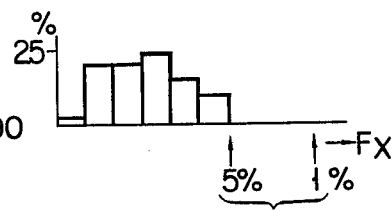
5%　1% ←Fx
SIGNIFICANT LEVEL
FIG. 4B
NORMAL EEG
GROUP
OBTAINED DURING
HYPERVENTILATION(HV)
N=90
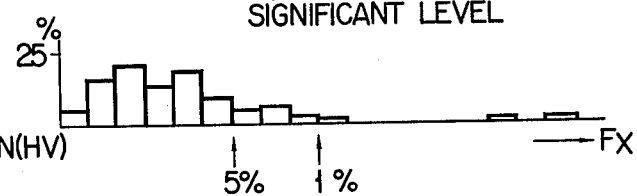
5%　1%　　→Fx
FIG. 4C
EPILEPTIC EEG
GROUP N=14
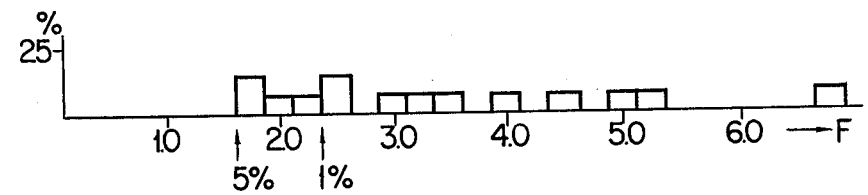
5% 1%
FIG. 5A1
FIG. 5B1
FIG. 5C1
FIG. 5A2
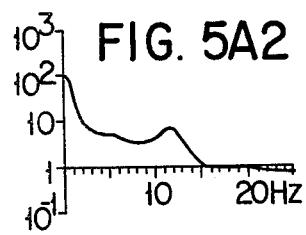
FIG. 5B2
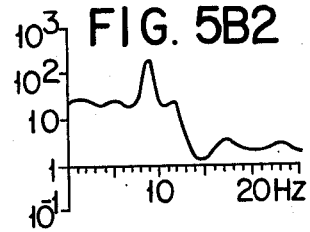
FIG. 5C2
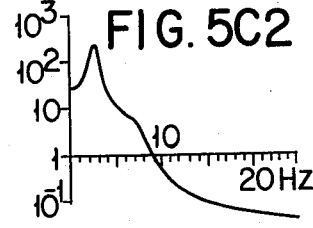
FIG. 5D1
FIG. 5D2
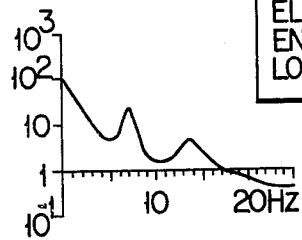
FIG. 3
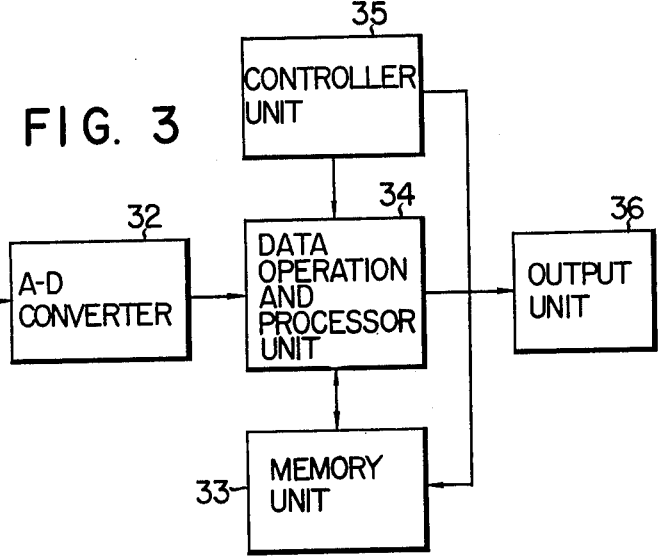

BRAIN WAVE ANALYZING SYSTEM AND METHOD

BACKGROUND OF THE INVENTION

This invention relates to a brain wave analyzing system and method for automatically identifying a spectrum pattern obtained by autoregressive model analysis of a brain wave.

Heretofore, diagnoses of brain waves have been made by observing irregular fluctuations of a brain wave appearing on an electroencephalograph or observing an electroencephalogram (hereinafter referred to as EEG) recorded on recording papers. Also, spectrum patterns obtained by Fourier-transform of the EEG was observationally used for the diagnoses. Accordingly, the decision-criteria have varied according to the experience, viewpoints, knowledge, etc. of diagnosticians, differentiating the analysis results from one another.

Thus, it has been proposed to substitute machines for means to make an observational decision of brain waves by men, though it is hardly possible for a machine completely to execute the intricate observation. Further the decision-criteria are still lacking in objectivity.

Accordingly, an object of this invention is to provide a brain wave analyzing system and method capable of automatically identifying brain wave spectrum patterns employing as parameters autoregressive coefficients obtained by quantitatively analyzing irregularly varying brain waves according to an autoregressive model.

SUMMARY OF THE INVENTION

In order to attain the above object, an embodiment of the system of the invention comprises an electroencephalograph for detecting brain waves; an A-D converter for converting the detected brain waves from the electroencephalograph into digital data; a data operation and processor unit for calculating and processing the digital data from the A-D converter; a memory unit for storing decision-criterion data for criticizing any brain wave supplied to the A-D converter and data obtained during the calculating and processing steps of the operation and processor unit; a controller unit for controlling the data operation and processor unit and the memory unit; and an output unit for displaying or recording the output of the data operation and processor unit. The memory unit is stored, as the decision-criterion data for any brain wave to be examined, with a mean vector $\overline{A}$, a variance vector C and at least one critical value $F_\alpha$ at a significant level $\alpha$ obtained from F-distribution. The mean vector $\overline{A}$ is the mean value of autoregressive coefficient vectors calculated by the data operation and processor unit from respective brain waves of a standard brain wave group consisting of K number of standard brain waves. The variance vector is calculated from the mean vector and the autoregressive coefficients. The data operation and process units calculates an L-dimensional row vector X of the brain wave to be examined from the autoregressive coefficients of the brain wave to be examined, calculates the distance $F_X$ between the row vector X and the mean vector $\overline{A}$, compares the value of the distance $F_X$ with the critical value $F_\alpha$ stored in the memory unit, and produces a decision output to indicate according to the result of the comparison whether or not the pattern of the brain wave to be examined has a significant level different from that of the standard brain wave group.

BRIEF DESCRIPTION OF THE DRAWINGS

FIG. 1A shows an example of EEG of a normal adult derived by Fz-Pz lead;

FIG. 1B shows an autoregressive power spectrum (solid line) of the EEG of FIG. 1A and the components (dashed lines) of this power spectrum;

FIG. 2 shows the percentage cumulative frequency distribution (black spots) of standardized autoregressive coefficients obtained from EEG's of 90 normal adults derived by Fz-Pz lead, dotted on a normal probability paper, together with the percentage cumulative frequency distribution (solid lines) based on the theoretical normal distribution;

FIG. 3 is a block diagram showing an embodiment of this invention;

FIGS. 4A, 4B and 4C show the frequency distribution of the distance $F_X$ between the vector of an EEG to be examined and the mean vector of a standard EEG group with respect to the cases of standard EEG group (CONT: FIG. 4A), the standard EEG group obtained during hyperventilation (HV: FIG. 4B), and epileptic EEG group (EP: FIG. 4C), respectively;

FIGS. 5A1, 5B1, 5C1 and 5D1 show each example of the normal EEG, the normal EEG obtained during hyperventilation, epileptic slow EEG, and epileptic fast EEG, respectively; and FIGS. 5A2, 5B2, 5C2 and 5D2 show power spectra corresponding to the EEG's of FIGS. 5A1, 5B1, 5C1 and 5D1, respectively.

DETAILED DESCRIPTION OF THE PREFERRED EMBODIMENT

Now the principle of this invention will be described with reference to the accompanying drawings. Brain waves which change momentarily as fluctuations of electrical brain action are formed of a part connected with some past activities of the brain and a part associated with no such activities. That is, in a discrete time series of a brain wave obtained at proper sampling intervals, the displacement $x_t$ from the average at time t may be represented by an autoregressive process having M number of orders and given as follows:

$$x_t = a_1 x_{t-1} + a_2 x_{t-2} + \ldots + a_m x_{t-m} + \ldots + a_M x_{t-M} + n_t \tag{1}$$

Here $a_m$, (m=1, 2, ... M) is an autoregressive coefficient indicating the degree of dependence on the past brain activities, while $n_t$ is a purely random variable of a variance $\sigma^2$. Substituting a backward shift operator B given by $$B^m x_t = x_{t-m}, \quad (m=0, 1, 2, \ldots) \tag{1a}$$

into equation (1), we obtain $$n_t \cdot G(B) = x_t, \text{ and} \tag{2}$$

$$n_t \longrightarrow \boxed{G(B)} \longrightarrow x_t \tag{2a}$$

A(B) (characteristic function) and G(B) (transfer function) may be obtained from the following equations.

$$A(B) = 1 - \sum_{m=1}^{M} a_m B^m \tag{3}$$

-continued $$G(B) = 1/A(B) \tag{4}$$

Equation (2) suggests that a random natural stimulation may be converted into a brain wave response $x_t$ (given as a displacement in equation (1)) by the activity (transfer function) of the brain site. Here the natural stimulation is one of stimuli that are given to various receptors under a variety of internal and external conditions, such as temperature, atmospheric pressure, gravity, body fluids, etc., without specially involving any artificial stimulation, whereby innumerable afferent impulse groups are supplied to the brain site in the vicinity of brain wave lead electrodes.

The power spectrum P(f) of $x_t$ (autoregressive process) as given by equation (1) is known to be given as the Fourier-transform of both members of equation (2). Namely, P(f) is $$P(f) = 2\sigma^2 n |G(e^{-i2\pi f})|^2 \tag{5}$$

where $0 \leq |f| < \frac{1}{2}$. It may easily be seen from equation (5) that the pattern of the power spectrum P(f) of the brain wave response $x_t$ or the inverse Fourier-transform of the power spectrum P(f) is determined by the autoregressive coefficient $\{a_m\}$ (equation (1)).

FIG. 1A shows an example of EEG of a normal adult derived by Fz-Pz lead, while FIG. 1B shows an autoregressive power spectrum (solid line) obtained by digitizing the EEG of FIG. 1A at sampling intervals of 20 msec and the components (dashed lines) of this power spectrum. From FIG. 1B it can be expected that the autoregressive coefficients $\{a_m\}$ exhibit normal distribution as regards many examples of EEG. Actual examination of the autoregressive coefficients $\{a_m\}$ for EEG's of 90 healthy adults derived by Fz-Pz lead reveals substantially normal distribution of the autoregressive coefficients $\{a_m\}$ as indicated by the black spots of FIG. 2.

Referring now to FIG. 2, the frequency distribution of the autoregressive coefficients $\{a_m\}$ of EEG's derived by Fz-Pz lead, as indicated by the black spots, is recorded in a normal probability paper. That is, $a_1, a_2, \ldots a_8$ are first to eighth order standardized autoregressive coefficients which are obtained by dividing the autoregressive coefficients $a_1, a_2, \ldots a_8$ of equation (1) by their corresponding standard deviation values for standardization. The illustrated oblique lines indicate the theoretical normal distribution (mean 0, standard deviation 1). As may be seen from FIG. 2, the black spots are distributed in close vicinity to these oblique lines.

Based on the results as shown in FIG. 2, this invention is intended for objectively deciding whether or not the power spectrum pattern of an optional brain wave is substantially identical with that of a standard brain wave group, e.g. a brain wave group of normal adults, by the method of multivariate analysis as mentioned later. Now there will be described the setting of the decision-criterion for the multivariate analysis method as well as the way of decision.

(1) Setting of decision-criterion

A standard brain wave group consisting of K number of standard brain waves is previously set, and L-dimensional row vectors $A_k$ as given by equation (6) are provided for the autoregressive coefficients obtained from those individual brain waves.

$$A_k = [a_{1k}\ a_{2k}\ \ldots,\ a_{Mk}\ \ldots,\ a_{Lk}],\ (k=1, 2, \ldots K) \tag{6}$$

Let us suppose $a_{mk}=0$ where $M < m \leq L$. Since the row vector $A_k$ may be considered subject to normal distribution if the number K of the brain waves is large, the mean vector $\overline{A}$ and variance vector C may be calculated according to $$\overline{A} = \frac{1}{K} \sum_{k=1}^{K} A_k, \text{ and} \tag{7}$$

$$C = \frac{1}{K} \sum_{k=1}^{K} (A_k - \overline{A})' \cdot (A_k - \overline{A}). \tag{8}$$

Subsequently, the inverse matrix $C^{-1}$ of the variance vector C is obtained. At the same time, the critical values at two suitable levels of significance $\alpha_1$ and $\alpha_2$ ($\alpha_2 > \alpha_1$) are obtained from the table of F-Distribution with degrees of freedom of L and K−L, the critical values of such levels being given as $F_{\alpha 1}$ and $F_{\alpha 2}$. Usually, $\alpha_1 = 0.01$ and $\alpha_2 = 0.05$.

(2) Way of decision (i) Decision on the pattern of an optional brain wave

Autoregressive coefficients for an optional brain wave to be examined is obtained, and an L-dimensional row vector X as given by equation (9) is obtained from such autoregressive coefficients.

$$X = [a_{1x}\ a_{2x}\ \ldots,\ a_{Lx}] \tag{9}$$

Therefore, the distance $F_X$ between the row vector X and the mean value $\overline{A}$ of the spectrum pattern of the standard brain wave group is obtained according to $$F_x = (K-L)K(K+1)^{-1}L^{-1}(X-\overline{A})' \cdot C^{-1}(X-\overline{A}) \tag{10}$$

If the power spectrum pattern of this optional brain wave is substantially identical with that of the standard brain wave group, it will exhibit F-distribution with degrees of freedom at L and K−L. Therefore, it is decided that the power spectrum pattern of this optional brain wave is substantially identical with that of the standard brain wave group when $F_X \leq F_{\alpha 2}$, that the former is different from the latter when $F_X > F_{\alpha 1}$, and that the former is on the border between the identical and different patterns when $F_{\alpha 1} < F_X \leq F_{\alpha 2}$.

(ii) Decision on an optional brain wave group

It is decided whether or not the pattern of a brain wave group consisting of J number of brain waves to be examined is different from that of the standard brain wave group. The respective autoregressive coefficients of these J number of brain waves are obtained, and L-dimensional row vectors $X_j$ of the jth brain wave ($j=1, 2, \ldots, J$) are obtained from these autoregressive coefficients, as given by equation (6a).

$$X_j = [a_{1xj}\ a_{2xj}\ \ldots,\ a_{Lxj}] \tag{6a}$$

where $j=1, 2, \ldots J$. Further, the mean vector $\overline{X}$ and variance vector $C_x$ of the row vectors $X_j$ of equation (6a) are obtained as follows:

$$\overline{X} = \frac{1}{J} \sum_{j=1}^{J} X_j \tag{7a}$$

$$C_x = \frac{1}{J} \sum_{j=1}^{J} (X_j - \overline{X})' \cdot (X_j - \overline{X}) \tag{8a}$$

Subsequently, the difference D between the mean vector $\overline{X}$ and the mean vector $\overline{A}$ of the standard brain wave group (refer to equation (7)) is obtained according to $$D = \overline{X} - \overline{A}$$

In this case, the distance $F_D$ between the brain wave group to be examined and the standard brain wave group may be given by $$F_D = \{(M-L-1)JK/ML\}D \cdot V^{-1} \cdot D' \qquad (10a)$$

where $M = J + K$ and $V = JC_x + KC$. If the pattern of the brain wave group to be examined belongs to that of the standard brain wave group (there is no significant difference between the two groups), the distance $F_D$ will be subject to F-distribution with degrees of freedom at L and $M - L - 1$. Here, in this F-distribution, suitable levels of significance $\alpha_1$ and $\alpha_2$ ($\alpha_2 > \alpha_1$) are determined, and the respective values of F-distribution for $\alpha_1$ and $\alpha_2$ are given as $F_{\alpha 1}$ and $F_{\alpha 2}$. Consequently, it is decided that the spectrum pattern of the brain wave group to be examined is substantially identical with that of the standard brain wave group when $F_D \leq F_{\alpha 2}$, that the former is different from the latter when $F_D \leq F_{\alpha 1}$, or that the former is on the border between the identical and different patterns when $F_{\alpha 2} < F_D \leq F_{\alpha 1}$.

Meanwhile, if only one level of significance is determined and given as $\alpha$, the critical value $F_\alpha$ may be obtained from F-distribution with degrees of freedom at L and $K - L$ in the case (i), while it may be obtained from F-distribution with degrees of freedom at L and $M - L - 1$ in the case (ii). Thus, it is decided that the pattern of the brain wave to be examined is different from that of the standard brain wave group when $F_X > F_\alpha$ or that the former belongs to the latter when $F_X \leq F_\alpha$. Further, it is decided that the brain wave group to be examined is different from that of the standard brain wave group when $F_D > F_\alpha$ or that there is no significant difference between these two groups when $F_D \leq F_\alpha$.

FIG. 3 is a block diagram showing an embodiment of the brain wave analyzing system according to this invention. In FIG. 3 there are shown an electroencephalograph 31 for detecting brain waves of a subject, an A-D converter 32 for converting the detected brain waves into digital data, a memory unit 33 for storing the digital data from the A-D converter and also the results of operation at a data operation and processor unit as mentioned later as well as data to be used as the decision-criteria, for brain waves to be examined, and the data operation and processor unit 34 for calculating and processing the data stored in the memory unit 33 according to the aforesaid calculating equations, comparing the results of such operation with the decision-criterion data, and identifying the normality of the EEG recorded on the electroencephalograph 31. Further, numeral 35 denotes a controller for controlling the data operation and processor unit 34 and the memory unit 33, while 36 denotes an output unit for displaying or recording the information in the memory unit 33 or data operation and processor unit 34 controlled and read out by the controller 35.

Now there will be described the operation of the system shown in FIG. 3. The brain waves from the subject are detected by the electroencephalograph 31, and the detected brain waves are digitized by the A-D converter 32. The data operation and processor unit 34 finds the autocovariance of the digitized brain wave, which is used for determining the order M and coefficients $a_1, a_2, \ldots, a_m$ in the autoregressive process of the brain wave, and the distance $F_X$ given by equation (10) is obtained from such order and coefficients. Then, the distance $F_X$ is compared with the aforesaid critical value $F_\alpha$ of the level of significance, and thus the spectrum pattern of the subject brain wave is identified objectively and automatically.

That is, it is decided that the power spectrum pattern of the brain wave to be examined is substantially identical with that of the aforesaid standard brain wave group when $F_X \leq F_\alpha$ or that the former is different from the latter when $F_X > F_\alpha$. Thereafter, the result of such decision is displayed on the output unit 36. The memory unit 33 is used for storing and reading the data obtained during the operation process of the data operation and processor unit 34.

According to an embodiment of this invention, as described above, the L-dimensional row vectors $A_k$ (equation (6)) are obtained from the K sets of autoregressive coefficients of the standard brain wave group, and the mean vector $\overline{A}$ (equation (7)) is obtained from these row vectors. Further, the variance vector C of the standard brain wave group is obtained from the row vectors $A_k$ and mean vector $\overline{A}$. Moreover, the levels of significance $F_{\alpha 1}$ and $F_{\alpha 2}$ with degrees of freedom of L and $K - L$ from the table of F-distribution are predetermined as standard values. On the other hand, obtained is the autoregressive coefficient of the EEG to be examined, from which the L-dimensional row vectors X (equation (9)) of the EEG to be examined are obtained. Then, employing the data (K, $\overline{A}$, $C^{-1}$) on the standard EEG group and the data (L, X) on the EEG to be examined, the distance $F_X$ (equation (10)) between the L-dimensional row vector X and the mean vector $\overline{A}$ is obtained. By comparing the distance $F_X$ with the levels of significance $F_{\alpha 1}$ and $F_{\alpha 2}$ it is decided whether or not the pattern of the brain wave to be examined is substantially identical with that of the standard brain wave group. Thus, the brain wave to be examined may be identified objectively and automatically.

Now there will be described test examples to indicate the usefulness of the invention. As an example of the standard EEG group, there was employed an EEG group (CONT) derived by Fz-Pz lead from 90 normal adults with closed eyes, sitting and resting relaxed. Then, the same group of 90 EEG's subjected to hyperventilation (HV) and a group of 14 epileptic EEG's (EP) were analyzed by means of the system of the invention.

The EEG groups CONT, HV and EP are shown, respectively, in FIGS. 4A, 4B and 4C with the axes of abscissa and ordinate representing the distance $F_X$ obtained by equation (10) and the frequency distribution (%) of the distance $F_X$, respectively. With the level of significance $\alpha = 5\%$ it was decided that 0% of the EEG group (CONT, FIG. 4A) 8% of the standard EEG group subjected to hyperventilation (HV, FIG. 4B), and 100% of the epileptic EEG group (EP, FIG. 4C) had different power spectrum patterns from that of the standard brain wave group. When the two levels of significance $\alpha_1$ and $\alpha_2$ were set at 0.01 (1%) and 0.05 (5%), it was decided that the power spectrum patterns of 3 EEG's out of the HV group (FIG. 4B) were different from the standard EEG power spectrum pattern with $F_X > F_{0.01}$, while those of 4 EEG's were on the border with $F_{0.05} < F_X \leq F_{0.01}$. In the EP group (FIG.

4C) the patterns of 10 EEG's were decided to be different from that of the standard EEG group (FIG. 4A) with $F_X > F_{0.01}$, while those of the remaining 4 EEG's were decided to be on the border with $F_{0.05} < F_X \leq F_{0.01}$.

In decision on the EEG group to be examined with the distance $F_D$ given by equation (10a), it was decided that the mean power spectrum pattern of the 90 EEG's of the HV group exhibited no significant difference from that of the standard EEG group with $F_D < F_{0.05}$, while that of the 14 EEG's of the EP group exhibited considerable significant difference from that of the standard EEG group.

FIGS. 5A1, 5B1, 5C1 and 5D1 show each example of the normal EEG (standard EEG), EEG obtained during hyperventilation, epileptic EEG with slow wave pattern, and epileptic EEG with fast wave pattern. FIGS. 5A2, 5B2, 5C2 and 5D2 show power spectrum patterns corresponding to the EEG's of FIGS. 5A1, 5B1, 5C1 and 5D1, respectively. Among these drawings FIGS. 5A1 and 5A2 show a pattern similar to that of the mean spectrum of the standard EEG group—an example of the normal case where the distance $F_X$ is short. FIGS. 5B1 and 5B2, 5C1 and 5C2 and 5D1 and 5D2 show abnormal EEG's whose power spectrum patterns were decided to be different from the mean spectrum pattern of the standard EEG group.

According to the above-mentioned system of this invention, the decision on the brain waves can be standardized, so that the system may be used for wide applications, such as screening of epileptic or other abnormal brain waves, brain wave monitoring under anesthesia or after surgical operations on brains.

What we claim is:

1. A brain wave analyzing system, comprising:
   an electroencephalograph for detecting brain waves;
   an A-D converter coupled to said electroencephalograph for converting the detected brain waves from said electroencephalograph into digital data;
   a data operation and processor unit coupled to said A-D converter for calculating and processing said digital data from said A-D converter;
   a memory unit for storing decision-criterion data for criticizing any brain wave supplied to said A-D converter and data obtained during the calculating and processing steps of said operation and processor unit;
   a controller unit for controlling said data operation and processor unit and said memory unit; and
   an output unit coupled to said data operation and processor unit for displaying or recording the output of said data operation and processor unit;
   said memory unit including means for storing, as said decision-criterion data for any brain wave to be examined, a mean vector $\overline{A}$, a variance vector C and at least one significant level $F_\alpha$ obtained from F-distribution, said mean vector $\overline{A}$ being the mean value of autoregressive coefficient vectors calculated by said data operation and processor unit from respective brain waves of the standard brain wave group comprising K number of standard brain waves, said variance vector C being calculated as a function of said mean vector and said autoregressive coefficients, and said F-distribution being a distribution of a distance between said mean vector $\overline{A}$ and a row vector X obtained from a given brain wave belonging to said standard brain wave group;
   said data operation and processor unit including means for calculating an L-dimensional row vector X of the brain wave to be examined from the autoregressive coefficients of said brain wave to be examined, means for calculating the distance $F_X$ between said row vector X and said mean vector $\overline{A}$, means for comparing the value of said distance $F_X$ with said significant level $F_\alpha$ stored in said memory unit, and means responsive to said comparing means for producing a decision output to indicate according to the result of said comparison whether or not the pattern of said brain wave to be examined has a significant level different from that of said standard brain wave group.

2. A brain wave analyzing system according to claim 1, wherein:
   said memory unit stores, as said decision-criterion data for any brain wave to be examined, said mean vector $\overline{A}$, said variance vector C and two significant levels $F_{\alpha 1}$ and $F_{\alpha 2}$ ($F_{\alpha 2} > F_{\alpha 1}$) obtained from said F-distribution; and
   said comparing means of said data operation and processor unit compares the value of said distance $F_X$ with said significant levels $F_{\alpha 1}$ and $F_{\alpha 2}$ to produce a decision output for selectively indicating that the power spectrum pattern of said brain wave to be examined has no significant difference with respects that of said standard brain wave group when $F_X \leq F_{\alpha 2}$, that the power spectrum pattern of said brain wave to be examined has a significant difference with respect to that of said standard brain wave group when $F_X > F_{\alpha 1}$, and that the power spectrum pattern of said brain wave to be examined is on the border between said significant level which is not different from that of said standard brain wave group and said significant level which is different from that of said standard brain wave when $F_{\alpha 2} < F_X \leq F_{\alpha 1}$.

3. A brain wave analyzing system, comprising:
   an electroencephalograph for detecting brain waves;
   an A-D converter coupled to said electroencephalograph for converting the detected brain waves from said electroencephalograph into digital data;
   a data operation and processor unit coupled to said A-D converter for calculating and processing said digital data from said A-D converter;
   a memory unit for storing decision-criterion data for criticizing any brain wave group supplied to said A-D converter and data obtained during the calculating and processing steps of said operation and processor unit;
   a controller unit for controlling said data operation and processor unit and said memory unit; and
   an output unit coupled to said data operation and processor unit for displaying or recording the output of said data operation and processor unit;
   said memory unit including means for storing, as said decision-criterion data for any brain wave group to be examined, a mean vector $\overline{A}$, a variance vector C and at least one significant level $F_\alpha$ obtained from F-distribution, said mean vector $\overline{A}$ being the mean value of autoregressive coefficient vectors calculated by said data operation and processor unit from respective brain waves of a standard brain wave group comprising K number of standard brain waves, said variance vector C being calculated as a function of said mean vector and said autoregressive coefficients, and said F-distribution being a distribution of a distance between said mean vector $\overline{A}$ and a row vector X obtained from a given brain wave belonging to said standard brain wave group;

said data operation and processor unit including means for calculating an L-dimensional row vector $X_j$ and the mean vector $\overline{X}$ of said row vector $X_j$ from the autoregressive coefficients of the individual brain waves among a brain wave group to be examined which comprises J number of brain waves, means for calculating the difference value D between said mean vector $\overline{X}$ of said row vector and said mean vector $\overline{A}$ of said standard brain waves, means for calculating, using said difference value D, the distance $F_D$ between said mean vector $\overline{X}$ of said brain wave group to be examined and said mean vector $\overline{A}$ of said standard wave group, means for comparing the value of said distance $F_D$ with said significant level $F_\alpha$ stored in said memory unit, and means responsive to said comparing means for producing a decision output to indicate according to the result of said comparison whether or not the patterns of said brain wave group to be examined has a significant difference with respect to that of said standard brain wave group.

4. A brain wave analyzing system according to claim 3, wherein:

said memory unit stores, as said decision-criterion data for any brain wave group to be examined, said mean vector $\overline{A}$, said variance vector C and two critical values $F_{\alpha 1}$ and $F_{\alpha 2}$ ($F_{\alpha 1} < F_{\alpha 1}$) at significant levels $\alpha 1$ and $\alpha 2$ ($\alpha_2 > \alpha_1$) obtained from said F-distribution; and said comparing means of said data operation and processor unit compares the value of said distance $F_D$ with said critical values $F_{\alpha 1}$ and $F_{\alpha 2}$ to produce a decision output for selectively indicating that the power spectrum pattern of said brain wave group to be examined has no significant difference with respect to that of said standard brain wave group when $F_D \leq F_{\alpha 2}$, that the power spectrum pattern of said brain wave group to be examined has a significant difference with respect to that of said standard brain wave group when $F_D > F_{\alpha 1}$, and that the power spectrum pattern of said brain wave group to be examined on the border between said critical value $F_{\alpha 2}$ which is not different from that of said standard brain wave group and said critical value $F_{\alpha 1}$ which is different from that of said standard brain wave group when $F_{\alpha 2} < F_D \leq F_{\alpha 1}$.

5. Method for analyzing brain waves comprising:
(a) detecting K number of standard brain waves;
(b) converting said detected standard brain waves into digital data by means of an A-D (analogue-to-digital) converter;
(c) obtaining a mean vector $\overline{A}$ from said digital data, said mean vector $\overline{A}$ being the mean value of autoregressive coefficient vectors calculated from the digital data corresponding to said respective standard brain waves;
(d) obtaining a variance vector C calculated from said mean vector $\overline{A}$ and said autoregressive coefficients;
(e) setting a least one significant level $F_\alpha$ obtained from F-distribution, said F-distribution being a distribution of a distance between said mean vector $\overline{A}$ and a row vector X obtained from a given brain wave belonging to said standard brain waves;
(f) detecting a brain wave to be examined;
(g) converting said detected brain wave to be examined into digital data by means of said A-D converter;
(h) obtaining an L-dimensional row vector X of said brain wave to be examined from the autoregressive coefficients of the digital data corresponding to said brain wave to be examined;
(i) calculating the distance $F_X$ between said L-dimensional row vector X and said mean vector $\overline{A}$, said distance $F_X$ being calculated from said mean vector $\overline{A}$, said variance vector C and said L-dimensional row vector X; and
(j) comparing said distance $F_X$ with said significant level $F_\alpha$ for deciding whether said brain wave to be examined belongs to said standard brain waves.

6. Method for analyzing brain waves comprising:
(a) detecting K number of standard brain waves;
(b) converting said detected standard brain waves into digital data by means of an A-D (analogue-to-digital) converter;
(c) obtaining a mean vector $\overline{A}$ from said digital data, said mean vector $\overline{A}$ being the mean value of autoregressive coefficient vectors calculated from the digital data corresponding to said respective standard brain waves;
(d) obtaining a variance vector C calculated from said mean vector $\overline{A}$ and said autoregressive coefficients;
(e) setting two significant levels $F_{\alpha 1}$ and $F_{\alpha 2}$ ($F_{\alpha 1} < F_{\alpha 2}$) obtained from F-distribution, said F-distribution being a distribution of a distance between said mean vector $\overline{A}$ and a row vector X obtained from a given brain wave belonging to said standard brain waves;
(f) detecting a brain wave to be examined;
(g) converting said detected brain wave to be examined into digital data by means of said A-D converter;
(h) obtaining an L-dimensional row vector X of said brain wave to be examined from the autoregressive coefficients of the digital data corresponding to said brain wave to be examined;
(i) calculating the distance $F_X$ between said L-dimensional row vector X and said mean vector $\overline{A}$, said distance $F_X$ being calculated from said mean vector $\overline{A}$, said variance vector C and said L-dimensional row vector X; and
(j) comparing the value of said distance $F_X$ with said two significant levels $F_{\alpha 1}$ and $F_{\alpha 2}$ for deciding that said brain wave to be examined belongs to said standard brain waves when $F_X \leq F_{\alpha 2}$, that said brain wave to be examined does not belong to said standard brain waves when $F_X > F_{\alpha 1}$, and that it is impossible to determine whether said brain wave to be examined belongs to said standard brain waves when $F_{\alpha 2} < F_X \leq F_{\alpha 1}$.

7. Method for analyzing brain waves comprising:
(a) detecting K number of standard brain waves;
(b) converting said detected brain waves into digital data by means of an A-D (analogue to digital) converter;
(c) obtaining a mean vector $\overline{A}$ from said digital data, said mean vector $\overline{A}$ being the mean value of autoregressive coefficient vectors calculated from the digital data corresponding to said respective standard brain waves;
(d) obtaining a variance vector C calculated from said mean vector $\overline{A}$ and said autoregressive coefficients;

(e) setting at least one significant level $F_\alpha$ obtained from F-distribution, said F-distribution being a distritution of a distance between said mean vector $\overline{A}$ and a row vector X obtained from a given brain wave belonging to said standard brain waves;
(f) detecting J number of brain waves to be examined;
(g) conerting said brain waves to be examined into digital data by means of said A-D converter;
(h) obtaining an L-dimensional row vector $X_j$ of said brain waves to be examined from the autoregressive coefficients of the digital data corresponding to the individual brain waves to be examined;
(i) calculating a mean vector $\overline{X}$ of said L-dimensional row vectors $X_j$ from the autoregressive coefficients of the digital data corresponding to the individual brain waves to be examined;
(j) calculating the difference value D between said mean vector $\overline{X}$ of said L-dimensional row vectors $X_j$ and said mean vector $\overline{A}$ of said standard brain waves;
(k) calculating a distance $F_D$ between said mean vector $\overline{X}$ of said brain waves to be examined and said mean vector $\overline{A}$ of said standard brain waves, said distance $F_D$ being calculated by using said difference value D and said variance vector C; and
(l) comparing said distance value D with said significant level $F_\alpha$ for deciding whether said brain waves to be examined belong to said standard brain waves.

8. Method for analyzing brain waves comprising:
(a) detecting K number of standard brain waves;
(b) converting said detected brain waves into digital data by means of an A-D (analogue to digital) converter;
(c) obtaining a mean vector $\overline{A}$ from said digital data, said mean vector $\overline{A}$ being the mean value of autoregressive coefficient vectors calculated from the digital data corresponding to said respective standard brain waves;
(d) obtaining a variance vector C calculated from said mean vector $\overline{A}$ and said autoregressive coefficients;
(e) setting two significant levels $F_{\alpha 1}$ and $F_{\alpha 2}$ ($F_{\alpha 1} < F_{\alpha 2}$) at significant levels $\alpha 1$ and $\alpha 2$ ($\alpha 1 < \alpha 2$) obtained from F-distribution, said F-distribution being a distribution of a distance between said mean vector $\overline{A}$ and a row vector X obtained from a given brain wave belonging to said standard brain waves;
(f) detecting J number of brain waves to be examined;
(g) converting said brain waves to be examined into digital data by means of said A-D converter;
(h) obtaining an L-dimensional row vector $X_j$ of said brain waves to be examined from the autoregressive coefficients of the digital data corresponding to the individual brain waves to be examined;
(i) calculating a mean vector $\overline{X}$ of said L-dimensional row vectors $X_j$ from the autoregressive coefficients of the digital data corresponding to the individual brain waves to be examined;
(j) calculating the difference value D between said mean vector $\overline{X}$ of said L-dimensional row vectors $X_j$ and said mean vector $\overline{A}$ of said standard brain waves;
(k) calculating a distance $F_D$ between said mean vector $\overline{X}$ of said brain waves to be examined and said mean vector $\overline{A}$ of said standard brain waves, said distance $F_D$ being claculated by using said difference value D and said variance vector C; and
(l) comprising the value of said distance $F_D$ with said two significant levels $F_{\alpha 1}$ and $F_{\alpha 2}$ for deciding that said brain waves to be examined belong to said standard brain waves when $F_D \leq F_{\alpha 2}$, that said brain waves to be examined do not belong to said standard brain waves when $F_D > F_{\alpha 1}$, and that it is impossible to determine whether said brain waves to be examined belong to said standard brain waves when $F_{\alpha 2} - F_D \leq F_{\alpha 1}$.

* * * * *